United States Patent
Roeder et al.

(10) Patent No.: US 9,550,012 B2
(45) Date of Patent: Jan. 24, 2017

(54) TISSUE SCAFFOLDS HAVING BONE GROWTH FACTORS

(71) Applicant: University of Notre Dame du Lac, Notre Dame, IN (US)

(72) Inventors: Ryan K. Roeder, Granger, IN (US); Matthew J. Meagher, Notre Dame, IN (US); Robert J. Kane, South Bend, IN (US)

(73) Assignee: University of Notre Dame Du Lac, Notre Dame, IN (US)

( * ) Notice: Subject to any disclaimer, the term of this patent is extended or adjusted under 35 U.S.C. 154(b) by 0 days.

(21) Appl. No.: 14/452,422

(22) Filed: Aug. 5, 2014

(65) Prior Publication Data
US 2015/0132354 A1 May 14, 2015

Related U.S. Application Data

(60) Provisional application No. 61/862,107, filed on Aug. 5, 2013.

(51) Int. Cl.
| | |
|---|---|
| A61K 38/18 | (2006.01) |
| A61L 27/54 | (2006.01) |
| A61L 27/56 | (2006.01) |
| A61L 27/40 | (2006.01) |
| A61L 27/24 | (2006.01) |
| A61L 27/12 | (2006.01) |
| A61P 19/08 | (2006.01) |
| A61L 27/46 | (2006.01) |

(52) U.S. Cl.
CPC ............ *A61L 27/54* (2013.01); *A61K 38/18* (2013.01); *A61K 38/1866* (2013.01); *A61K 38/1875* (2013.01); *A61L 27/46* (2013.01); *A61L 27/56* (2013.01); *A61L 2300/414* (2013.01); *A61L 2430/02* (2013.01)

(58) Field of Classification Search
None
See application file for complete search history.

(56) References Cited

U.S. PATENT DOCUMENTS

| | | |
|---|---|---|
| 6,296,667 B1 | 10/2001 | Johnson et al. |
| 7,163,691 B2 | 1/2007 | Knaack et al. |
| 7,758,882 B2 | 7/2010 | Roeder et al. |
| 8,022,040 B2 | 9/2011 | Bertozzi et al. |
| 8,293,486 B2 | 10/2012 | Kaplan et al. |
| 8,303,973 B2 | 11/2012 | Daniloff et al. |
| 8,309,518 B2 | 11/2012 | Schense et al. |
| 8,318,674 B2 | 11/2012 | Schense et al. |
| 8,328,876 B2 | 12/2012 | Behnam et al. |
| 2003/0031698 A1 | 2/2003 | Roeder et al. |
| 2004/0258729 A1* | 12/2004 | Czernuszka .......... A61L 27/227 424/426 |
| 2011/0081324 A1 | 4/2011 | Chmielewski et al. |
| 2011/0190209 A1* | 8/2011 | Culbertson ...... A61K 47/48215 514/13.7 |
| 2012/0076773 A1* | 3/2012 | Sargeant ............. A61L 24/0031 424/130.1 |
| 2012/0253470 A1 | 10/2012 | Guze et al. |

FOREIGN PATENT DOCUMENTS

| | | |
|---|---|---|
| WO | 2008106625 A2 | 9/2008 |
| WO | 2011109834 A2 | 9/2011 |
| WO | 2012118843 A1 | 9/2012 |

OTHER PUBLICATIONS

Kempen et al., Biomaterials, 2009, vol. 30(14):2816-2825.*

* cited by examiner

*Primary Examiner* — Xiaozhen Xie
(74) *Attorney, Agent, or Firm* — Haukaas Fortius PLLC; Michael H. Haukaas

(57) ABSTRACT

The invention provides a novel composite bone graft system utilizing a porous collagen scaffold having a matrix impregnated with calcium phosphate particles and more than one bioactive agent, one of which is conjugated to the matrix. The graft system exhibits increased mechanical strength and osteogenic properties by providing sites for tissue attachment and propagation. The bioactive agents are delivered to the scaffold via different mechanisms to enable sequential and sustained release of the bioactive agents over time.

18 Claims, 6 Drawing Sheets

TISSUE SCAFFOLDS HAVING BONE GROWTH FACTORS

RELATED APPLICATIONS

This application claims priority under 35 U.S.C. §119(e) to U.S. Provisional Patent Application No. 61/862,107 filed Aug. 5, 2013, which is incorporated herein by reference.

GOVERNMENT SUPPORT

This invention was made with government support under W81XWH-09-1-0741 awarded by the United States Army Medical Research and Material Command (USAMRMC). The government has certain rights in the invention.

BACKGROUND OF THE INVENTION

Bone defects and fractures have spurred widespread research into repairing and regenerating tissue and bone formation. Many synthetic bone graft substitutes have been developed which provide suitable osteoconductivity. See Calori G M, Mazza E, Colombo M, Ripamonti C. The use of bone-graft substitutes in large bone defects: any specific needs? *Injury* 2011; 42 Suppl 2:S56-63; Greenwald a S, Boden S D, Goldberg V M, Khan Y, Laurencin C T, Rosier R N. Bone-graft substitutes: facts, fictions, and applications. *J Bone Joint Surg Am* 2001; 83-A Suppl:98-103; and Zimmermann G, Moghaddam A. Allograft bone matrix versus synthetic bone graft substitutes. *Injury* 2011; 42 Suppl 2:S16-21. However, improvements in the osteoinductivity and osteogenicity of synthetic bone graft substitutes could provide more rapid tissue repair and, consequently, an increase in the number of successful unions. See Giannoudis P V, Calori G M, Begue T, Schmidmaier G. Bone regeneration strategies: current trends but what the future holds? *Injury* 2013; 44 Suppl 1:S1-2; and Carson J S, Bostrom M P G. Synthetic bone scaffolds and fracture repair. *Injury* 2007; 38 Suppl 1:S33-7.

The osteoinductivity and osteogenicity of bone tissue engineering substitutes could be improved by the delivery of appropriate growth factors to healing tissue along biologically relevant timelines. See Lauzon M-A, Bergeron E, Marcos B, Faucheux N. Bone repair: new developments in growth factor delivery systems and their mathematical modeling. *J Control Release* 2012; 162:502-20. While several studies have indicated that the delivery of growth factors, the conjugation of growth factors, prolonged growth factor release, and the delivery of more than one growth factor, may under certain conditions hasten and enhance bone tissue repair, none have achieved sequential and sustained release of growth factors along biologically relevant timelines. See Kempen D H R, Lu L, Heijink A, Hefferan T E, Creemers L B, Maran A, et al. Effect of local sequential VEGF and BMP-2 delivery on ectopic and orthotopic bone regeneration. *Biomaterials* 2009; 30:2816-25; Boerckel J D, Kolambkar Y M, Dupont K M, Uhrig B, Phelps E, Stevens H Y, et al. Effects of protein dose and delivery system on BMP-mediated bone regeneration. *Biomaterials* 2011; 32:5241-51; Chung Y-I, Ahn K-M, Jeon S-H, Lee S-Y, Lee J-H, Tae G. Enhanced bone regeneration with BMP-2 loaded functional nanoparticle-hydrogel complex. *J Control Release* 2007; 121:91-9; Geuze R, Theyse L. A Differential Effect of BMP-2 and VEGF Release Timing on Osteogenesis at Ectopic and Orthotopic Sites in a Large Animal Model. *Tissue Eng Part A* 2012:1-34; and Ferrara N. VEGF and the quest for tumour angiogenesis factors. *Nat Rev Cancer* 2002; 2:795-803.

There is a need to improve the rate of non-union in long bone fractures. Estimates indicate that 5-10% of bone fractures exhibit impaired healing, either delayed unions or non-unions, and that many of these result from critical size defects. See Calori G M, Mazza E, Colombo M, Ripamonti C. The use of bone-graft substitutes in large bone defects: any specific needs? *Injury* 2011; 42 Suppl 2:S56-63; Frölke J, Patka P. Definition and classification of fracture non-unions. *Injury* 2007; 38S:S19-22; Tzioupis C, Giannoudis P. Prevalence of long-bone non-unions. *Injury* 2007; 44; and Calori G, Albisetti W, Agus A, Iori S, Tagliabue L. Risk factors contributing to fracture non-unions. *Injury* 2007: S11-S18.

Limitations in utilizing autograft and allograft sources to promote bone repair and regeneration have led to extensive research in synthetic bone graft substitutes and bone tissue engineering scaffolds aimed at preserving the advantages of autografting and allografting while overcoming their limitations and constraints. See Zimmermann G, Moghaddam A. Allograft bone matrix versus synthetic bone graft substitutes. *Injury* 2011; 42 Suppl 2:S16-21; O'Brien F J. Biomaterials & scaffolds for tissue engineering. *Mater Today* 2011; 14:88-95; Salgado A J, Coutinho O P, Reis R L. Bone tissue engineering: state of the art and future trends. *Macromol Biosci* 2004; 4:743-65; and Szpalski C, Wetterau M, Barr J, Warren S M. Bone Tissue Engineering: Current Strategies and Techniques—Part I: Scaffolds 2012; 18.

Numerous patent applications and papers have been published in this field. See U.S. patent application Ser. No. 12/039,666; WO 2011/109834; U.S. Pat. No. 6,296,667; WO 2012/118843; U.S. Pat. No. 8,022,040; U.S. patent application Ser. No. 13/435,259; U.S. Pat. No. 7,758,882; Kempen, D. H., et al. 2009. Effect of local sequential VEGF and BMP-2 delivery on ectopic and orthotopic bone regeneration. *Biomaterials,* 30: 2816-2825; U.S. Pat. No. 8,328, 876; U.S. Pat. No. 7,163,691; U.S. Pat. No. 8,318,674; U.S. Pat. No. 8,309,518; U.S. Pat. No. 8,303,973; US Pat. No. 8,293,486; and EP2300033.

Current methods for treating bone defects and fractures via the delivery of VEGF and BMP-2 do not sufficiently achieve sustained release of the growth factors along the physiologically-relevant timelines necessary to enhance spatio-temporal growth factor expression. This is because conventional methods rely on passive adsorption of growth factors on the scaffold biomaterial surface or sponge-like absorption of a growth factor-containing solution within scaffold pore spaces. The conventional methods release a single, super-physiological bolus dose of growth factors, which delivers an excess of growth factors earlier than needed for optimum repair and/or regeneration of tissue and/or bone. Further, conventional methods do not allow for coordinated, sequential delivery of growth factors within the fracture gap and thus cannot take advantage of synergistic effects that might arise from sequential delivery of complimentary growth factors. Moreover, clinical, passive adsorption of BMP-2 in spinal fusion applications has not only resulted in a lack of temporal control of BMP-2 release, but also a lack of spatial control and delivery has been seen. Occasionally the conventional mechanisms have been implicated in negative outcomes including extradiscal, ectopic, or heterotopic ossification and an associated risk of edema.

Therefore, notwithstanding the advancements in the field, many limitations remain in current treatments that contribute to impaired healing, delayed bony unions and non-unions.

Thus, there exists a need for improved synthetic bone graft substitutes. The invention described herein provides such an article and methods of using it. The synthetic bone graft substitutes described herein enable sequential and sustained release of growth factors and provide a powerful tool to promote and expedite successful bony union in otherwise problematic fracture non-unions and bone defects.

SUMMARY

The invention provides a novel composite bone graft system utilizing a porous collagen scaffold impregnated with calcium phosphate particles and more than one bioactive agent, one of which is conjugated to the matrix. The graft system exhibits increased mechanical strength and osteogenic properties by providing sites for tissue attachment and propagation. The bioactive agents are delivered to the scaffold to enable sequential and sustained release of the bioactive agents over time. One mechanism for loading a bioactive agent on a scaffold can provide long-term release and another mechanism for loading a bioactive agent on a scaffold can provide short-term release.

Accordingly, the system can be tailored to release the bioactive agents along biologically relevant timelines. One aspect of the invention provides a tunable tissue scaffold comprising a matrix and at least two bioactive agents delivered to the matrix via different mechanisms. The scaffold can be employed as an implantable synthetic bone graft substitute to promote the repair and/or regeneration of tissue and/or bone in a tissue of a patient having a bone defect or fracture. The at least two bioactive agents may comprise A and B, wherein bioactive agent A has been delivered to the matrix by conjugation and a protein-ligand interaction between biotin and a biotin-binding protein, and bioactive agent B has been delivered to the matrix by (i) conjugation and a pH labile covalent linkage or (ii) non-conjugation and passive adsorption. The pH labile covalent linkage may comprise a hydrazone linkage for conjugation of the bioactive agent B to a calcium-chelating moiety. Alternatively, the non-conjugated bioactive agent B may be encapsulated within a biodegradable polymer, hydrogel or protein matrix and delivered to the matrix via passive adsorption.

In still another aspect of the invention, one of the bioactive agents has been biotinylated and conjugated to the matrix, and (i) the matrix has been biotinylated and conjugated to the biotin-binding protein or (ii) the matrix has incorporated the biotin-binding protein without conjugation.

Another aspect of the invention utilizes growth factors VEGF and BMP-2 as the bioactive agents. VEGF and BMP-2 are each released from the matrix in a sequential and sustained manner, which may be tailored to coincide along naturally occurring biologically processes of angiogenesis and osteogenesis during bone repair and regeneration.

In still yet another aspect of the invention, the matrix comprises cross-linked collagen fibrils and about 0-80 vol % of calcium phosphate reinforcements.

In yet another aspect of the invention, a method of enhancing tissue and/or bone repair and/or regeneration in a patient in need thereof is provided by introducing the tissue scaffold as described herein into a tissue of the patient.

In yet one more aspect of the invention, a method of preparing a tunable tissue scaffold matrix is taught comprising:

(a) mixing calcium phosphate reinforcements into a collagen slurry;

(b) (i) incorporating a biotin-binding protein into the calcium phosphate-collagen slurry and compression molding the calcium phosphate-collagen-biotin-binding protein slurry to form a matrix; or (b) (ii) compression molding the calcium phosphate-collagen slurry to form a matrix, biotinylating the matrix, and conjugating a biotin-binding protein to the matrix;

(c) biotinylating BMP-2 or VEGF;

(d) adding an effective amount of the biotinylated BMP-2 or VEGF to the matrix to obtain a desired load of biotinylated BMP-2 or VEGF conjugated to the matrix; and (e) delivering BMP-2 or VEGF to the matrix by (1)
(i) mixing an effective amount of the non-biotinylated BMP-2 or VEGF with collagen fibrils in a biodegradable polymer, hydrogel solution or protein matrix; and
(ii) impregnating the matrix with the BMP-2 or VEGF containing biodegradable polymer, hydrogel solution or protein matrix via capillary action or centrifugation;

or (2)
(i) covalently conjugating BMP-2 or VEGF to one terminus of a hydrazone-containing chemical compound;
(ii) covalently conjugating a calcium-chelating moiety to the other terminus of the hydrazone-containing chemical compound; and
(iii) adding an effective amount of hydrazone-conjugated BMP-2 or VEGF to the matrix to obtain a desired load of hydrazone-conjugated BMP-2 or VEGF.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
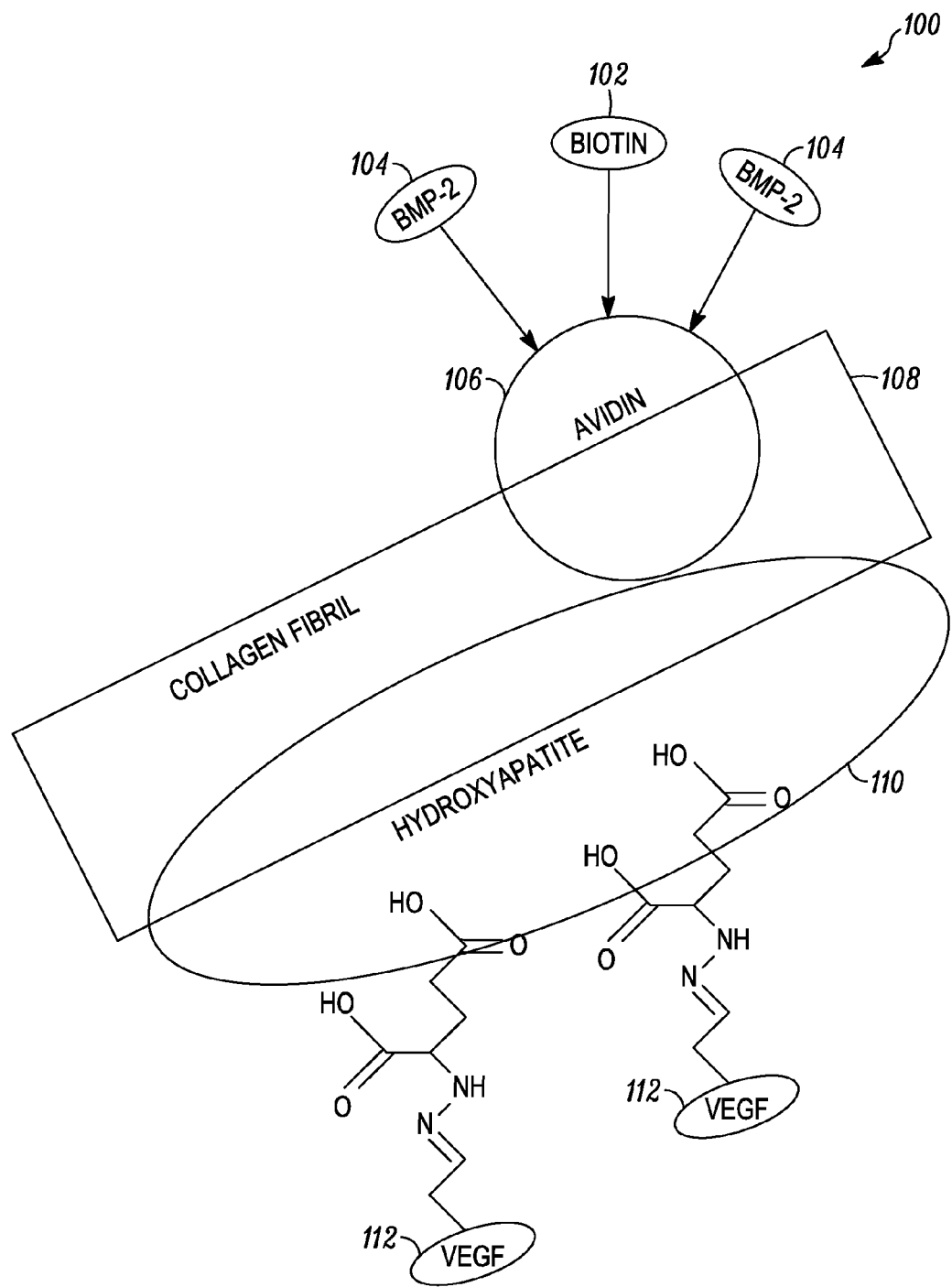
FIG. 1 illustrates a schematic diagram showing conjugation of a first pharmaceutical biomolecule or growth factor to hydroxyapatite using glutamic acid functional groups with an acid-labile hydrazone linkage and conjugation of a second pharmaceutical biomolecule or growth factor to collagen using biotinylated avidin, according to an embodiment.

The invention described herein enables one to independently tailor the in vivo release kinetics of multiple bioactive agents to control growth factor dosage and release kinetics. For example, one can design the scaffold to promote and support osteogenesis with one growth factor and independently deliver another growth factor to support angiogenesis. Endogenous fracture repair mechanisms require growth factors to stimulate and coordinate the cellular activity necessary for osteogenesis. However, these growth factors are autocrine and paracrine molecular signals, which are localized to the healing front of advancing mesenchymal stem cells (MSCs). VEGF and BMP-2 are two bone growth factors useful for treating bone defects and fractures. Dispersion of VEGF and BMP-2 throughout the scaffold will make these growth factors available throughout the fracture gap, not merely at the front of recovery. The expanded spatial distribution of VEGF and BMP-2 as compared to endogenous fracture healing can encourage simultaneous angiogenesis and osteogenesis throughout the scaffold by supporting cellular invasion.

In addition to hastening the infiltration of endothelial cells and osteogenic cells into the fracture gap, growth factor loading via the invention can allow for the release of growth factors along biologically relevant timelines, which is not possible using current delivery methods. Further, immobilization of growth factors can offer additional advantages. For example, immobilization of VEGF leads to the formation of smaller, structured capillary networks while the release of soluble VEGF results in the formation of large, leaky vasculature in vivo. Further, immobilization of BMP-2 prevents release of BMP-2 into non-osseous tissues and increases the local concentration of BMP-2 available to infiltrating cells facilitating the use of smaller loaded doses of BMP-2 than current technologies.

This approach for coordinated delivery of VEGF and BMP-2 could be subsequently adapted to accommodate additional molecules of interest, including other growth factors, small molecule inhibitors, or even genes. However, the coordinated delivery of VEGF and BMP-2 offers a fast path for clinical translation by providing an "off-the-shelf" clinical solution to the repair of large segmental bone defects. These novel synthetic bone graft substitutes can perform predictably in vivo as they are free of the variability associated with cells introduced to the scaffold prior to implantation, have no associated immunologic concerns, and can be readily available to surgeons in sufficient quantities whenever a bone graft is required. These novel synthetic bone graft substitutes are superior, or at least equivalent, to the current clinical standard, autograft, in terms of osteoconductivity and osteoinductivity, and do not possess an inherent risk of donor site morbidity.

The invention described herein comprises a synthetic bone graft substitute for sequential and sustained release of angiogenic and osteogenic growth factors to promote healing of a critical size bone defect. For example, hydroxyapatite-collagen (HA-Col) scaffolds functionalized with VEGF and BMP-2 delivered to the matrix via different mechanisms enable the optimization of release kinetics to promote, coordinate and support angiogenesis and osteogenesis. Tunability of sustained release can be achieved by utilizing two separate mechanisms, including conjugation.

DEFINITIONS

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment disclosed in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a bioactive agent" includes a plurality of such bioactive agents, so that a bioactive agent X includes a plurality of bioactive agents X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least two" are readily understood by one of skill in the art, particularly when read in context of its usage. For example, the phrase "at least two bioactive agents" refers to two, three, or more bioactive agents.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is within the capacity of persons skilled in the art. The term "effective amount" is intended to include an amount of an agent described herein, or an amount of a combination of agents described herein, e.g., that is therapeutically effective to treat or prevent an injury, disease or disorder, or to mediate the symptoms of the injury, disease or disorder, in a host. Thus, an "effective amount" generally means an amount that provides the desired effect.

The terms "treating", "treat" and "treatment" include (i) preventing an injury, disease, pathologic or medical condition from occurring (e.g., prophylaxis) or worsening; (ii) inhibiting the injury, disease, pathologic or medical condition or arresting its development; (iii) relieving or promoting the healing of the injury, disease, pathologic or medical condition; and/or (iv) diminishing symptoms associated with the injury, disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

Useful dosages of the agents described herein can be determined by evaluating their in vitro activity and in vivo activity in animal models. Methods for the extrapolation of effective dosages in mice, and other animals, to humans are known to the art. The effective amount of an agent, or an active salt or derivative thereof, required for use in treatment will vary not only with the particular agent or salt selected but also with the route of administration, the nature of the condition being treated, and the age and condition of the patient, and will be ultimately be at the discretion of an attendant physician or clinician.

The invention provides therapeutic methods of treating bone fractures and defects in a mammal, which involve administering to a mammal having such bone fractures or defects an effective amount of an agent or composition described herein. A mammal includes a primate, human, rodent, canine, feline, bovine, ovine, equine, swine, caprine, bovine and the like. The ability of an agent or composition of the invention to treat bone fractures and defects may be determined by using assays well known to the art.

An osseous tissue is a major structural and supportive connective tissue of the body, where bone tissue forms a rigid part of the bone organs that make up the skeletal system, as known to those having ordinary skill in the art.

A bony defect is any size defect in a bone of a human or an animal that does not heal spontaneously in a reasonable amount of time, as known to those having ordinary skill in the art.

A scaffold is a natural or artificial (synthetic) support that maintains tissue contour, as known to those having ordinary skill in the art.

Bone grafting is a surgical procedure by which new bone (transplanted from a donor site to a recipient site) or a replacement material is placed into spaces between or around broken bone (fractures) or holes in bone (defects) to aid in healing. Bone grafting replaces missing bone and is generally used to repair bone fractures that are extremely complex, pose a significant risk to the patient or fail to heal properly. Bone graft is also used to help fusion between vertebrae, correct deformities or provide structural support for fractures of the spine. In addition to fracture repair, bone graft is used to repair defects in bone caused by birth defects, traumatic injury, or surgery for bone cancer.

Bone generally has the ability to regenerate completely but requires a very small fracture space or some sort of scaffold to do so. Bone grafts may be autologous (bone harvested from the patient's own body, often from the iliac crest), allograft (cadaveric bone usually obtained from a bone bank), or synthetic (often made of hydroxyapatite or other naturally occurring and biocompatitble substances) with similar mechanical properties to bone. Most bone grafts are expected to be reabsorbed and replaced as the natural bone heals over a few months' time.

The principles involved in successful bone grafts include osteoconduction (guiding the reparative growth of the natural bone), osteoinduction (encouraging undifferentiated cells to become active osteoblasts), and osteogenesis (living bone cells in the graft material contribute to bone remodeling). Osteogenesis only occurs with autografts.

Biocompatible means something that is compatible with living tissue or a living system, that is, something that is not toxic, injurious or physiologically reactive and does not cause an immunological rejection, as known to those having ordinary skill in the art.

A tissue scaffold includes a tissue engineering scaffold and/or a synthetic bone graft substitute usable for enhancing repair and/or regeneration of tissue and/or bone in a patient in need thereof.

A tunable tissue scaffold means a scaffold containing bioactive agents which can be regulated to tailor the amount, timing and/or duration of the release of bioactive agents from the scaffold. A tunable tissue scaffold is useful for implantation in a tissue of a patient suffering a bone defect or fracture for sustained and/or sequential release of the bioactive agents along biologically relevant timelines to the tissue and/or bone of a patient in need thereof.

Embodiments

In one embodiment a tunable tissue scaffold is provided, which is useful as an implantable synthetic bone graft substitute to promote the repair and/or regeneration of tissue and/or bone in a tissue of a patient having a bone defect or fracture. The scaffold comprises a matrix and at least two bioactive agents delivered to the matrix via different mechanisms.

The at least two bioactive agents may comprise A and B wherein, bioactive agent A has been delivered to the matrix by conjugation and a protein-ligand interaction between biotin and a biotin-binding protein, and bioactive agent B has been delivered to the matrix by (i) conjugation and a pH labile covalent linkage or (ii) non-conjugation and passive adsorption.

The biotin-binding protein may be selected from the group consisting of streptavidin, avidin, neutravidin, and non-glycosylated, tetrameric biotin-binding proteins.

The at least two bioactive agents may be selected from the group consisting of vascular endothelial growth factors (VEGFs), biogenic amines, bone morphogenetic proteins (BMPs), insulin-like growth factors (IGFs), fibroblast growth factors (FGFs), transforming growth factor beta (TGF-β), platelet-derived growth factors (PDGFs), nerve growth factors (NGFs), connective tissue growth factors (CTGFs), and epidermal growth factors (EGFs).

One way to deliver the bioactive agent to the matrix includes biotinylating the bioactive agent and conjugating it to the matrix, wherein (i) the matrix has been biotinylated and conjugated to the biotin-binding protein or (ii) the matrix has incorporated the biotin-binding protein without conjugation.

Another separate and distinct way to deliver the bioactive agent to the matrix includes (i) conjugation and a pH labile covalent linkage or (ii) non-conjugation and passive adsorption. The pH labile covalent linkage comprises a hydrazone linkage for conjugation of the bioactive agent B to a calcium-chelating moiety. The calcium-chelating moiety may be carboxylate, phosphonate, bisphosphonate or other negative charge density agent (for promoting a link to the calcium phosphate in the matrix). In certain embodiments, the bisphosphonate calcium-chelating moiety is alendronate or glutamic acid.

Another embodiment of the invention utilizes growth factors VEGF and BMP-2 as the bioactive agents A and B. VEGF and BMP-2 are each released from the matrix in a sequential and sustained manner, which may be tailored to coincide along naturally occurring biologically processes of angiogenesis and osteogenesis during bone and/or tissue repair and/or regeneration. In one particular embodiment, bioactive agent A is BMP-2 and bioactive agent B is VEGF.

In still another embodiment, the non-conjugated bioactive agent B has been encapsulated within a biodegradable polymer, hydrogel or protein matrix. In a particular embodiment, bioactive agent B is encapsulated in a hydrogel.

About 0.1 μg to 100 μg of each bioactive agent may be delivered to the matrix.

The tunable scaffold may be tailored to provide for efficient sequential and sustained release of the bioactive agents along biologically relevant timelines. This is a powerful tool as one agent can be tailored to release over a short timeline, while another agent can be tailored to release over a longer timeline. The different mechanisms in delivering the agents to the matrix provide the tools for adjusting the release of the agents to a desired timeline. For example, BMP-2 may be released from the matrix in vivo over a biologically relevant timeline extending from between about 7 and 56 days. This can be seen as a sustained, long timeline. In contrast, VEGF may released from the matrix in vivo over a biologically relevant timeline extending from between about 1 and 28 days. This can be seen as a sustained, short timeline. In addition, peak release of the bioactive agents can be controlled. For example, the peak release of BMP-2 from the matrix in vivo may be tailored to occur between about 21 and 28 days, while independently, the peak release of VEGF from the matrix in vivo may be tailored to occur between about 10 and 14 days.

Having multiple mechanisms for delivering multiple bioactive agents to the matrix gives the user a variety of ways to individually tailor the release of each agent along a desired timeline to maximize efficacy of the scaffold. The release of an agent can be tuned and tailored by binding some concentration of the agent by a short-term release mechanism and a different concentration of the same agent by a long-term release mechanism. An analogous type of tuning can be accomplished with a second agent. For example, we have described herein a long-term release mechanism and two short-term release mechanisms. One could load bioactive agent A to the matrix via any one, two or three of the release mechanisms, and independently, load bioactive agent B to the matrix via any one, two or three of the release mechanisms. This flexibility in tailoring the release of the agents via various combinations of release mechanisms is useful for optimizing release of the agents along biologically relevant timelines.

Methods of loading the bioactive agents into the scaffold are described herein. It is understood that the order of the steps in the methods may not necessarily proceed along the described path and can be interchanged when appropriate. For example, biotinylation of a bioactive agent may be undertaken in an earlier or later step than has been specifically described herein.

The matrix may comprise cross-linked collagen fibrils and about 0-80 vol % of calcium phosphate reinforcements. In one embodiment, the matrix comprises about 20-60 vol % of calcium phosphate reinforcements. The calcium phosphate reinforcements may be hydroxyapatite or β-tricalcium phosphate. The morphology of the calcium phosphate reinforcements may be in the form of spheres or whiskers. The matrix may have about 65-99 vol % of porosity, pore diameters of about 100-1000 μm, and a compressive modulus of greater than about 100 kPa. In one embodiment, the matrix has a porosity level of about 75-95%, pore diameters of about 200-600 μm, and a compressive modulus of about 200-1000 kPa. In a particular embodiment, the scaffold comprises a 0.8-2.0 MPa compression mold having cross-linked collagen fibrils, 0-80% volume of hydroxyapatite whisker reinforcements, streptavidin, a porosity level of 65-99%, pore diameters of 100-1000 ☐m, and a compressive modulus of 200-1000 kPa.

A particular embodiment provides a tunable tissue scaffold comprising a matrix and at least two bioactive agents comprising vascular endothelial growth factor (VEGF) and bone morphogenetic protein 2 (BMP-2), wherein the matrix comprises cross-linked collagen, hydroxyapatite reinforcements and a biotin-binding protein;

BMP-2 has been biotinylated and conjugated to the matrix, and
  (i) the matrix has been biotinylated and conjugated to the biotin-binding protein; or
  (ii) the matrix has incorporated the biotin-binding protein without conjugation;
and
VEGF
  (i) has been conjugated via a hydrazone linkage to a calcium-chelating moiety selected from the group consisting of glutamic acid and bisphosphonates; or
  (ii) has not been conjugated and has been encapsulated within a biodegradable polymer, hydrogel, or protein matrix.

In one way to prepare the tunable tissue scaffold, VEGF or BMP-2 is biotinylated; streptavidin is infused into a concentrated collagen fibril slurry; hydroxyapatite reinforcement whiskers are mixed into the collagen-streptavidin slurry to achieve at least 40% volume of hydroxyapatite reinforcement whiskers; the hydroxyapatite-collagen-streptavidin slurry is compression molded at 0.8-2.0 MPa to form the matrix; an effective amount of the biotinylated VEGF or BMP-2 is added drop-wise to the matrix to obtain a desired concentration conjugated to the matrix; the unbiotinylated VEGF or BMP-2 is mixed into a collagen-containing hydrogel solution; and an effective amount of the unbiotinylated VEGF or BMP-2/collagen-containing hydrogel solution is impregnated into the matrix via capillary action to obtain a desired concentration conjugated to the matrix.

The invention described herein includes a hydroxyapatite-collagen scaffold prepared through the use of compression molding and porogen leaching, which exhibits improved architecture and mechanical properties compared to the limitations imposed by freeze-dried scaffolds. The hydroxyapatite-collagen scaffolds also exhibit increased strut thicknesses. Hydroxyapatite-collagen scaffolds can be tailored to possess generally 75-95 vol % porosity, up to approximately 80 vol % of bioactive hydroxyapatite reinforcements, and a compressive modulus of at least 100 kPa, usually from 200-1000 kPa. The scaffolds exhibit recoverable elastic deformation upon cyclic loading up to 50% strain, which enable surgical handling, fixation, and bearing osteogeneic loads during healing. Scaffold pores are approximately 200-500 μm and interconnected.

A method is described herein to conjugate at least one bioactive agent (e.g., pharmaceutical biomolecule or growth factor) to the scaffold. VEGF and BMP-2 are useful bioactive agents. VEGF is expressed by mesenchymal stem cells in the vicinity of intramuscular implantation of BMP-2 in a collagen carrier.

In one embodiment of the invention, a method of conjugating more than one pharmaceutical biomolecule or growth factor is described. First, BMP biotinylation is accomplished by conjugating biotin to BMP via an NHS-mediated mechanism. The scaffold is prepared for BMP conjugation by incorporating a biotin-binding protein directly into the scaffold matrix or by biotinylating the scaffold matrix via an NHS-mediated mechanism and allowing a biotin-binding protein to associate with the biotinylated matrix. The biotinylated BMP is then exposed to the biotin-binding protein decorated matrix to allow association between the biotinylated BMP and the biotin-binding protein. The conjugation of glutamic acid to VEGF by an acid-labile hydrazone linkage is accomplished in order to enable chelation of the VEGF-glutamic acid construct to hydroxyapatite crystals in the collagen scaffolds. VEGF can be released via two mechanisms, in vivo acid-catalyzed hydrolysis of the hydrazone linkage or by dissociation of glutamic acid from hydroxyapatite. This approach enables sustained release of VEGF and independent control of its release kinetics relative to BMP-2.

A connective open foam collagen matrix can be disrupted by the addition of type I bovine collagen in the collagen matrix to a solution of HCl, NaOH and PBS and use of a tissue homogenizer. A scaffold system can be prepared by infusion of avidin into the hydroxyapatite collagen matrix at a mass ratio of up to about 1:1. A scaffold system synthesized with a biotin-binding protein can be prepared by mixing a plurality of hydroxyapatite reinforcement whiskers into a concentrated collagen fibril slurry or by biotinylation of the scaffold matrix and association with a biotin-binding protein.

The hydroxyapatite-collagen slurry with or without a biotin-binding protein can be compression molded. Cross-linking of the scaffold system can be accomplished with the addition of EDC and NHS in ethanol.

The scaffold system may be placed in a solution containing biotinylated BMP-2 at an appropriate molar ratio to conjugate it with the incorporated avidin, forming rhBMP-2, followed by a solution containing a VEGF-glutamic acid construct, such that the scaffold systems is conjugated with rhBMP-2 and VEGF-glutamic acid. The scaffold can be used as an enabling system for the sequential and sustained release of VEGF followed by rhBMP-2, or vice versa, wherein the sequential and sustained release of VEGF and rhBMP-2 over a time scale coincides with biological timelines of natural bone regeneration. In certain situations, it may be advantageous to decrease or increase the timed release to promote faster and more efficient healing of the defect.

Hydroxyapatite-reinforced collagen scaffolds conjugated with VEGF and BMP-2 were synthesized and growth factors by two distinct and independent conjugation mechanisms were verified. The in vitro release kinetics of the hydroxyapatite-reinforced collagen scaffolds for conjugation were measured and compared to passive absorption of pharmaceutical biomolecules or growth factors.

The hydroxyapatite-collagen scaffolds described herein exhibit improved mechanical properties and will better support bone regeneration than currently existing technologies. In contrast, conventional freeze-dried hydroxyapatite-collagen scaffolds do are not able to support osteogenic loading and thus, their utility is limited. The use of distinct and separate conjugation mechanisms for VEGF and BMP-2 enables independent control over the release kinetics and dose of each growth factor, in contrast to a bolus release from passive absorption.

A synthetic bone graft substitute is described herein, which allows for sustained release of a first pharmaceutical biomolecule or growth factor, followed by sustained release of a second pharmaceutical biomolecule or growth factor. This sequential and sustained release of two bioactive agents coincides with biological timelines of natural bone regeneration (unless it is determined that it is better to decrease or increase the timelines). Scaffolds with at least two pharmaceutical biomolecules or growth factors can exhibit increased osteoinductive bone formation after ectopic (subcutaneous) implantation compared to conventional applications which utilize passively absorbed growth factors. Providing conjugation of at least one pharmaceutical biomolecule or growth factor to collagen scaffolds reinforced with hydroxyapatite enables sustained and sequential sustained release of the growth factors over time. The invention remedies the current limitations of bolus release from passive absorption. The conjugation of at least two pharmaceutical biomolecules or growth factors to hydroxyapatite-collagen scaffolds exhibits an improved architecture and mechanical properties compared to conventional freeze-dried scaffolds.

Growth factors include peptides and proteins that stimulate the growth and/or differentiation of cells via the interaction of the growth factors with specific cell surface receptors, where growth factor's play an integral role in the repair and regeneration of tissues. Growth factors can be used to stimulate the repair of various tissues and organs, such as bone, cartilage, mucosa and skin. Growth factors enhance repair through the stimulation of angiogenesis at the repair site. For exogenous growth factors to be effective in stimulating repair, they should be retained at the site requiring repair and protected from inactivation, sequestration or degradation.

Examples of growth factors include, but are not limited to, transcription factors, bone morphogenetic proteins (BMPs), vascular endothelial growth factors (VEGFs), transforming growth factor beta (TGF-β), insulin-like growth factors (IGFs), fibroblast growth factors (FGFs), platelet derived growth factors (PDGFs), and others known in the art.

The terms bone morphogenetic protein and bone morphogenic protein are used interchangeably, abbreviated as BMP, and refer to any member of the bone morphogenetic protein subfamily of the transforming growth factor beta (TGF-β) superfamily of growth and differentiation factors, including BMP-2, BMP-3 (also known as osteogenin), BMP-3b (also known as growth and differentiation factor 10, GDF-10), BMP-4, BMP-5, BMP-6, BMP-7 (also known as osteogenic protein-1, OP-1), BMP-8 (also known as osteogenic protein-2, OP-2), BMP-9, BMP-10, BMP-11 (also known as growth and differentiation factor 8, GDF-8, or myostatin), BMP-12 (also known as growth and differentiation factor 7, GDF-7), BMP-13 (also known as growth and differentiation factor 6, GDF-6), BMP-14 (also known as growth and differentiation factor 5, GDF-5), and BMP-15. The terms bone morphogenetic protein, bone morphogenic protein and BMP encompass allelic variants of BMPs, function conservative variants of BMPs, and mutant BMPs that retain BMP activity. The BMP activity of such variants and mutants can be confirmed by any conventional method.

BMP can be BMP-2, BMP-4, BMP-5, BMP-6, BMP-7, BMP-8 or BMP-9. In certain embodiments, the BMP is BMP-2, BMP-4 or BMP-7. The BMP may be a mammalian BMP (e.g., mammalian BMP-2 or mammalian BMP-7). In a particular embodiment, the BMP is a human BMP (hBMP) (e.g., hBMP-2 or hBMP-7) and the second growth factor is a vascular endothelial growth factor (VEGF).

The delivery of at least two bioactive agents (e.g., pharmaceutical biomolecules or growth factors) to hydroxyapatite-reinforced collagen scaffolds, wherein at least one of the agents is conjugated to the scaffold, enables sequential and sustained release of the at least two pharmaceutical biomolecules or two growth factors over time, which coincides with the biological timelines of natural bone regeneration. The scaffold described herein exhibits an improved architecture with mechanical properties compared to current freeze-dried scaffolds. The presently disclosed methods and materials enhance the efficacy of reinforced scaffolds by improving the retention of at least two bioactive agents at sites of implantation, while maintaining growth factor activity. The bioactive agents can be used for delivering growth factor activity to help repair and regenerate bone. The dual delivery of bioactive agents can also be used in any other desired location in a body, where controlled sequential and sustained release of each agent is needed.

The tissue scaffolds disclosed herein are suitable for implantation. In one aspect of the invention, at least one surface of the scaffold is provided with at least two exogenous growth or biologically active factors having a therapeutic effect and/or clinical activity.

The tissue scaffold described herein can be introduced into a body by surgical or non-surgical methods. The scaffold is a biological or artificial tissue engineering carrier matrix for tissue-regenerating in a patient in need thereof. The scaffold can be a biocompatible scaffold, a bioactive scaffold and/or a biodegradable scaffold. In most circumstances, a biodegradable scaffold is needed. The term scaffold is not limited to any form and may, for instance, be in the form of a more or less rigid object or in the form of an amorphous material. Examples of inorganic scaffold materials include, but are not limited to calcium phosphate matrices (CaP) and hydroxyapatite (HA) matrices. CaP, sintered HA, bioactive glasses and bioactive ceramics form bone-like apatite on their surfaces in the living body, which bond to the living bone and exhibit high bioactivity and biocompatibility.

Hydroxyapatite has the advantage of being osteoconductive and bioactive. All the scaffold materials may be used in different forms, such as in the form of blocks, foams, sponges, granules, cements, implant coatings, and other forms not mentioned herein and may be combined with organic/inorganic materials or ceramics. The various forms may be obtained by extrusion, injection molding, solvent casting, leaching methods, compression molding and rapid prototyping (including 3D Printing, Multi-phase Jet Solidification, and Fused Deposition Modeling (FDM)), and other methods not mentioned herein.

The scaffold described herein can provide vascularization on the scaffold material when it is implanted, which supports the normal wound healing response of the body. The cells can be introduced at a time that the body would normally recruit them to start the tissue repair process. It can be advantageous for the cells to survive after implantation, since vascularization has already occurred and the cells can be introduced at a time during which the body would normally start to recruit them from surrounding tissues.

The term wound-healing response is the process associated with the cellular cascades of wound healing, which is brought about by injury and the subsequent disturbance of the homeostatic events due to injury to tissues or organs as a result of implantation of a biomaterial, prosthesis or medical device into a vertebrate body.

FIG. 1 illustrates a schematic diagram 100 showing the conjugation of a first pharmaceutical biomolecule or growth factor 112, such as a VEGF growth factor, to a hydroxyapatite 110. The biomolecule or growth factor 112 is conjugated using a glutamic acid functional group with an acid-labile hydrazone linkage. The figure shows the conjugation of a second pharmaceutical biomolecule or growth factor 104, such as a BMP-2 growth factor, to a collagen fibril 108 using an avidin 106 with a biotin 102.

The first pharmaceutical biomolecule or growth factor 112 may be, but is not limited to, vascular endothelial growth factors (VEGFs), biogenic amines, glycosaminoglycans (perlecan, versican, etc.), glycoproteins (erythropoietin), hormones (parathyroid hormone), and others bioactive agents used in the art. A biogenic amine is a biomolecule with one or more amine groups.

The second pharmaceutical biomolecule or growth factor 104 is conjugated to the collagen 108 using a biotin-binding protein 106. The second pharmaceutical biomolecule or growth factor 104 includes, but is not limited to, bone morphogenetic proteins (BMPs), insulin-like growth factors (IGFs), fibroblast growth factors (FGFs), transforming growth factor beta (TGF-β), platelet-derived growth factors (PDGFs), nerve growth factors (NGFs), connective tissue growth factors (CTGFs), epidermal growth factors (EGFs), and other bioactive agents known in the art.

In one embodiment, the hydroxyapatite 110 reinforcement particles may be any suitable calcium phosphate reinforcement particles including, but not limited to, alpha-tricalcium phosphate, beta-tricalcium phosphate, hydroxyapatite, and others known in the art.

In another embodiment, more than two pharmaceutical biomolecules may be implemented.

The connective tissue scaffold composition shown in the figure has a concentration of collagen fibrils 108 comprising a collagen matrix (not shown). The collagen matrix may be disposed proximal to a bone in need of repair or may be disposed proximal to any tissue in need of repair in other embodiments. At least two pharmaceutical biomolecules or growth factor may be conjugated to collagen matrix.

The first pharmaceutical biomolecule or growth factor is VEGF 112 and the second growth factor is BMP-2 104. The first pharmaceutical biomolecule or growth factor (VEGF) 112 may be conjugated to the collagen 108 by hydroxyapatite 110 using a glutamic acid functional group with an acid-labile hydrazone linkage. Different means of conjugation known in the art for the pharmaceutical biomolecules may be implemented.

To prepare a hydroxyapatite-collagen reinforced scaffold, hydroxyapatite 110 reinforcement particles may be first added to a suspension of concentrated collagen fibrils 108 in an aqueous medium to form a suspension. The suspension can be mechanically stirred, typically with a tissue homogenizer. Afterwards, the reinforced collagen slurry is a viscous liquid containing evenly dispersed reinforced particles.

A porogen material (which may be removed from the collagen 108 by dissolution in a suitable solvent) can be added into the slurry and mixed by any means until it is uniformly distributed throughout, with the volume of the porogen being allowed to range from approximately 0-95% of the total scaffold volume. In certain embodiments, the porogen volume is from 60-90% to help ensure interconnected porosity. The viscosity of the slurry helps prevent the porogen from settling out of solution. Examples of acceptable porogen materials include, but are not limited to, salts, cellulose, paraffin, polysaccharides, poly-α-hydroxy esters, and those known in the art. Porogen particles can be of any size and morphology.

Microspheres can be produced using a conventional method and fractionated to a size of approximately 300-425 μm using a sieve.

The porogen-containing collagen 108 slurry can be concentrated by filtration (vacuum or pressure, or any conventional method) to reduce the total solvent content. The final porogen-containing material has an approximate putty-like consistency and can be molded into a desired shape. The collagen-porogen putty can be further consolidated and dehydrated under an applied pressure from approximately 1-100 MPa.

Methods of consolidation may include, but are not limited to, compression molding, isostatic pressing, injection molding, extrusion processes, and other methods known in the art. The consolidation step may also be used to form the shape of an implant. The consolidation step aims at removing excess liquid and decreasing the density of the reinforced collagen. In this step, the fluid component can be reduced to less than approximately 50% of the material volume, where the resultant reinforced collagen 108 material can exhibit a density comparable to the extracellular matrix of a target physiological tissue. Bone tissue is used for reinforced collagen 108 scaffolds and tendon/ligament tissue is used for pure collagen scaffolds. The collagen 108 material can then be separated into struts by the porogen particles.

The porogen may be leached from the material using a suitable solvent, where a suitable solvent refers to one in which the porogen is soluble but the collagen 108 is not. Examples of suitable solvents for a paraffin porogen include, but are not limited to, xylene, hexane and others known in the art. Stirring, elevated temperature and changing the solvent bath may be used to speed the process.

Collagen materials 108 may be cross-linked by chemical cross-linking using gluteraldehyde or ethylene di-carbodiimide (EDC), dehydrothermal processing, ultraviolet or gamma radiation, or any other suitable method. Cross-linking is generally performed after porogen leaching. Cross-linking chemicals requiring an aqueous solution can cause swelling of the collagen scaffold before cross-linking can "lock in" the scaffold architecture. To avoid this problem, non-aqueous cross-linking chemicals are utilized, such as EDC in ethyl alcohol.

Typically, a cross-linking procedure involves submerging the collagen scaffold in a solution of approximately 5-10 mM EDC and NHS at an EDC/NHS ratio of approximately 1:1 to approximately 4:1. The scaffolds may be immersed in the EDC/NHS solution for approximately 2-5 hours and then rinsed to remove any unreacted EDC/NHS. The degree of cross-linking is controlled by the ratio of EDC:NHS:collagen and the reaction time. Once unreacted agents are rinsed, the scaffold may be sterilized and implanted. The scaffolds can be hydrated in sterile physiological saline prior to in vitro cell culture or implantation.

In one embodiment, a hydroxyapatite-collagen scaffold exhibiting improved architecture and mechanical properties (compared to the limitations imposed by the freeze-dried scaffolds) has been developed through the use of compression molding and porogen leaching, which increases the strut thickness. Scaffolds can be tailored to possess approximately 75-95% porosity, approximately 0-80 vol % bioactive hydroxyapatite 110 reinforcements, and a compressive modulus of approximately 200-1000 kPa. The scaffolds can exhibit recoverable elastic deformation upon cyclic loading up to approximately 50% strain, which helps enable surgical handling, fixation and bearing osteogeneic loads during healing. Scaffold pores may be approximately 200-500 μm and interconnected.

A method is disclosed herein to conjugate a first pharmaceutical biomolecule or growth factor (VEGF 112) with a second pharmaceutical biomolecule or growth factor (BMP-2 104).

A method of BMP-2 104 biotinylation can be accomplished with a well-established protocol. Biotin 102 can be conjugated to rhBMP-2 by mixing the protein with approximately 50 mM $NaHCO_3$ at a pH of 8.0 and incubating with equimolar amounts of EZ-linksulfo-NHS-LC-biotin for approximately 30 minutes at room temperature. Excess biotin 102 can be trapped by the addition of 10 mM tris/HCl at approximately pH 8.5 (5% v/v) and biotinylated rhBMP-2 can be captured in approximately 1 mM HCl via dialysis. Biotinylation generally does not disrupt BMP-2 104 function due to the small size of biotin 102.

A method of VEGF-glutamic acid conjugation involves glutamic acid conjugation to VEGF 112 via an acid-labile hydrazone linkage in order to enable chelation of the VEGF-glutamic acid construct to hydroxyapatite crystals in the collagen scaffolds. The solvent can be evaporated and the product can be washed with ethyl acetate to remove excess reactant. This method allows for VEGF 112 to be chelated to hydroxyapatite crystals in the scaffold via a pH triggered cleavable hydrazone linkage between glutamic acid and VEGF 112. Glutamic acid possesses the ability to chelate positively charged calcium ions in hydroxyapatite 110 due to the large density of negative charge localized in the carboxylate groups. Hydrazone linkages are generally stable at physiological pH, but the rate of hydrolysis gradually decreases with a decrease in pH below approximately 7.4, as is typically found at wound healing sites. Thus, VEGF 112 can be released via two mechanisms, in vivo acid-catalyzed hydrolysis of the hydrazone linkage, followed by dissociation of glutamic acid from hydroxyapatite. This approach can generally enable sustained release of VEGF 112 and independent control of its release kinetics relative to BMP-2 104.

A method is disclosed herein for preparing mechanically robust scaffolds synthesized with the addition of avidin 106. Collagen fibrils 108 are prepared using a tissue homogenizer to generally disrupt a collagen gel prepared at an approximate 37° C. overnight from soluble type I bovine collagen 108 at a concentration of approximately 3.2 mg/mL in a solution of 0.01 M HCl adjusted to an approximate physiological pH and ionic strength by the addition of an appropriate amount of approximately 1M NaOH and 10× PBS. The collagen fibrils 108 may be concentrated by centrifugation to approximately 160 mg/mL collagen 108.

Scaffolds containing avidin 106 may be prepared by infusing avidin 106 into the collagen gel at a mass ratio of no more than approximately 1:1, where gelation occurs in less than approximately 30 minutes.

Single crystal hydroxyapatite whisker reinforcements approximately 18×2 μm 110 can be prepared using a chelate decomposition method.

Paraffin microspheres can be prepared by solidifying emulsified paraffin droplets and size fractionating them to approximately 300-425 μm using a shaker sieve. Scaffolds may be prepared by mixing hydroxyapatite reinforcements 110 into the concentrated collagen fibril slurry at approximately 60% hydroxyapatite volume. Paraffin microspheres can be subsequently mixed into the slurry using a spatula in an amount determined to produce approximately 85% porosity by volume. The slurry can be compression molded at approximately 1 MPa in a 4 mm diameter dye. Scaffolds can then be subsequently dried at approximately 37° C. for 24-48 hours and leached of paraffin in a graded series of hexane/ethanol solutions for at least approximately 6 hours each.

Scaffolds can be cross-linked in approximately 20 mM EDC and approximately 8 mM NHS in 80% ethanol, with pH adjusted to approximately 7.4 with 0.1 HCl, for approximately 12 hours under gentle agitation. After cross-linking, scaffolds may be washed and stored in ethanol until further use. Optimal cross-linking conditions lead to a controlled degradation rate and optimal changes in the porosity and thickness of the scaffolds.

Verification of growth factor conjugation may include, but is not limited to methods such as, mass spectroscopy and MALDI-MD with hydrogen/deuterium exchange, and others used by one of ordinary skill in the art. The amount of VEGF 112 and BMP-2 104 either conjugated or absorbed within the scaffolds can be quantified by measuring supernatant concentrations via ELISA.

In vitro release kinetics can be tested on the hydroxyapatite-reinforced collagen scaffolds with both conjugated and absorbed growth factors. The scaffolds can be re-suspended in approximately 5 mL of approximately 0.1% BSA in PBS at generally 37° C. The buffer can be removed and replaced at selected time points, where the concentration of BMP-2 104, VEGF 112, and BSA in the release buffer can be measured by ELISA at desired time points until the protein is no longer measured in the buffer. The scaffolds can then be digested in approximately 0.1 mg/mL collagenase for approximately 12 hours and the residual protein will be measured.

Figure 2:
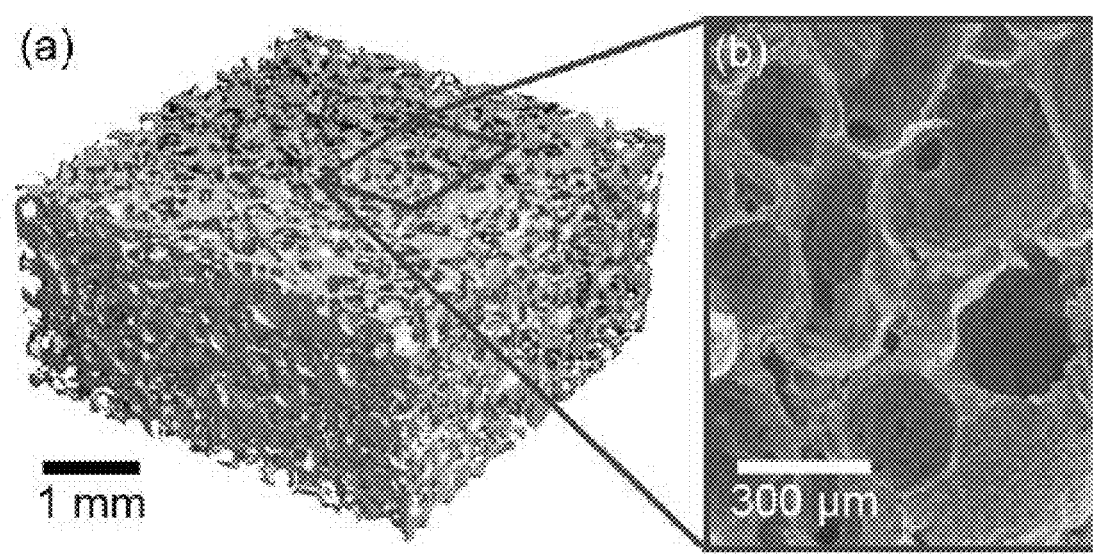
FIG. 2 illustrates a segmented micro-CT reconstructed of a porous collagen scaffold with hydroxyapatite reinforcements, according to an embodiment. (a) Micro-CT of a collagen scaffold with 90 vol % porosity and 80 vol % hydroxyapatite reinforcements, and (b) SEM micrograph showing the scaffold and pore interconnections more closely.

FIG. 2 illustrates a micro-CT reconstruction showing the architecture and an SEM micrograph showing pore interconnections of a porous scaffold 200 at high magnification. The scaffold 200 comprises hydroxyapatite reinforcement whiskers disposed throughout in up to approximately 80 vol % based on the total volume of the scaffold material and comprises an open foam porous architecture. The scaffold 200 includes a plurality of pores having a diameter of approximately 200 to 500 μm based on the total volume of the collagen matrix and a porosity of approximately 75 to 95% based on the total volume of the collagen matrix. The scaffold 200 comprises a compressive modulus of 200 to 1000 kPa.

Figure 3:
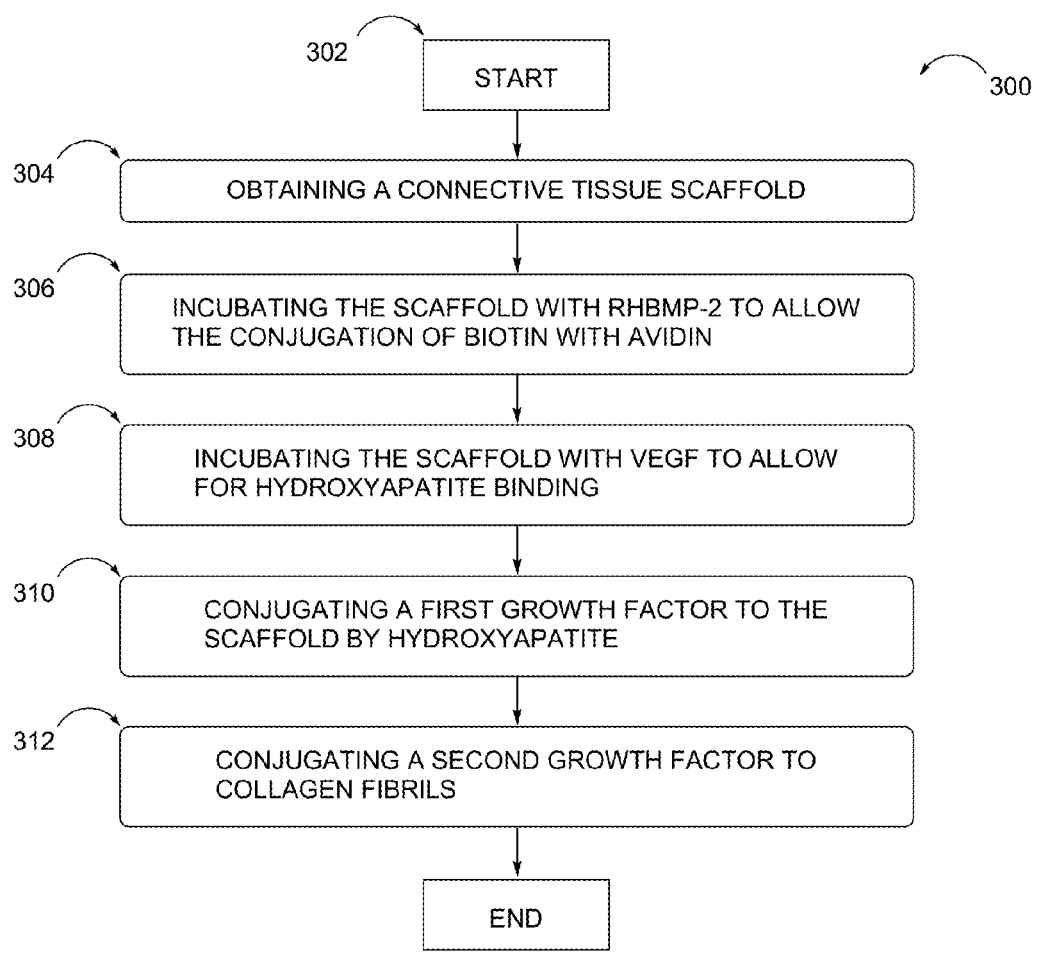
FIG. 3 illustrates a logic flow diagram for conjugating two growth factors to a connective tissue scaffold.

FIG. 3 illustrates a flow diagram for a process 300, a connective tissue scaffold with the initial start 302 of the method steps involved in the method for the conjugation of one or more pharmaceutical biomolecule or growth factors to a connective tissue scaffold.

The process 300 involves obtaining a connective tissue scaffold 304, wherein the connective tissue scaffold comprises an open foam porous architecture containing a concentration of collagen fibrils, which form a collagen matrix. A connective open foam collagen matrix may be disrupted by use of a tissue homogenizer and the addition of about 3.2 mg/mL type I bovine collagen to a solution of generally 0.01 M HCl, approximately 1.0 M NaOH, and about 10× PBS.

A method for providing mechanically robust scaffolds synthesized with the addition of avidin involves collagen fibrils being concentrated by centrifugation to approximately 160 mg/mL collagen. The process 300 involves the infusion of avidin into the connective open foam hydroxyapatite collagen matrix at a mass ratio of approximately 1:1, wherein gelation may occur in approximately less than thirty minutes. A plurality of hydroxyapatite reinforcements may be mixed into a concentrated collagen fibril slurry at about 60% hydroxyapatite volume.

Single crystal hydroxyapatite whisker reinforcements (approximately 18×2 μm) can be prepared using a chelate decomposition method known in the art. Paraffin microspheres can be prepared by solidifying emulsified paraffin droplets and size fractionating them to about 300-425 μm using a shaker sieve. Paraffin microspheres can be subsequently mixed into the slurry using a spatula in an amount determined to be approximately 85% porosity by volume. The slurry can be compression molded at about 1 MPa in an approximate 4 mm diameter dye. Scaffolds can be subsequently dried at approximately 37° C. for about 24-48 hours and leached of paraffin in a graded series of hexane/ethanol solutions for generally 6 hours each.

Scaffolds can be cross-linked in approximately 20 mM EDC and 8 mM NHS in about 80% ethanol, with pH adjusted to approximately 7.4 with approximately 0.1 HCl, for about 12 hours under gentle agitation. After cross-linking, scaffolds may be washed and stored in ethanol until further use. Optimal cross-linking conditions can lead to controlled degradation rates and optimal changes in the porosity and thickness of the scaffolds.

It can be appreciated that in alternative embodiments, varying types of reinforcement particles may be used, including, but not limited to, carbonated calcium hydroxyapatite, dicalcium phosphate dihydrate (DCPD), octacalcium phosphate (OCP), beta-tricalcium phosphate (beta-TCP), calcium hydroxyapatite (HA), biphasic calcium phosphate (BCP), anhydrous dicalcium phosphate (DCPA), anhydrous monocalcium phosphate (MCPA), alpha-tricalcium phosphate (alpha-TCP), tetracalcium phosphate, monocalcium phosphate monohydrate (MCPM), amorphous calcium phosphate (ACP), and others known in the art.

In process block 306, the conjugation of biotin may occur to an rhBMP-2 protein by mixing rhBMP-2 protein with approximately 50 mM NaHCO$_3$ at about pH 8.0 and incubating with equimolar amounts of EZ-linksulfo-NHS-LC-biotin for generally 30 minutes at room temperature. Excess biotin can be trapped by the addition of approximately 10 mM tris/HCl at about pH 8.5 (5% v/v) and biotinylated rhBMP-2 can be captured in approximately 1 mM HCl via dialysis. Biotinylation does not generally disrupt BMP-2 function due to the small size of biotin.

The process block 308 involves incubating the scaffold with VEGF to allow for hydroxyapatite binding to the scaffold. The process block 310 involves conjugating VEGF to the scaffold by hydroxyapatite. A method of VEGF-glutamic acid conjugation can involve glutamic acid conjugation to VEGF via an acid-labile hydrazone linkage in order to enable chelation of the VEGF-glutamic acid construct to hydroxyapatite crystals in the collagen scaffolds. The method allows for VEGF to be chelated to hydroxyapatite crystals in the scaffold via a pH triggered cleavable hydrazone linkage between glutamic acid and VEGF. Glutamic acid can possess the ability to chelate positively charged calcium ions in hydroxyapatite due to the large density of negative charge localized in the carboxylate groups.

Hydrazone linkages can be stable at physiological pH, but the rate of hydrolysis generally gradually decreases with a decrease in pH below approximately 7.4, as is found at wound healing sites. Thus, VEGF can be released via two mechanisms, in vivo acid-catalyzed hydrolysis of the hydrazone linkage, followed by dissociation of glutamic acid from hydroxyapatite. This approach can enable sustained release of VEGF and independent control of its release kinetics relative to BMP-2.

The process block 312 involves the conjugation of a BMP-2 to the collagen fibrils. The scaffold system can be placed in a solution containing mesenchymal stem cells involving biotinylated BMP-2 at an appropriate molar ratio to allow conjugation with the incorporated avidin, forming the BMP-2 followed by a solution containing a VEGF-glutamic acid construct, such that the scaffold systems can be conjugated with BMP-2 and the VEGF-glutamic acid.

The scaffold system can be used as an enabling system for the sequential and sustained release of a first pharmaceutical biomolecule or growth factor (VEGF) followed by a second pharmaceutical biomolecule or growth factor (BMP-2), where the sequential and sustained release of VEGF and BMP-2 over a time scale coincides with natural bone regeneration biological timelines.

To investigate the growth factor loading, the scaffolds can be placed in a solution containing biotinylated BMP-2 at an appropriate molar ratio to bind with the incorporated avidin, followed by placing the scaffold in a solution containing the VEGF-glutamic acid construct, such that scaffolds can be conjugated with BMP-2 and VEGF. The avidin-collagen ratio, growth factor solution concentrations, and soak times can be varied to investigate the effects on growth factor loading. Growth factors can also be passively absorbed by soaking hydroxyapatite-collagen scaffolds in solutions of BMP-2 and VEGF for comparison of burst release to the sustained release of conjugated growth factors.

Tunability of sustained release can be achieved by utilizing two separate mechanisms, including conjugation. The first mechanism involves the impregnation of a soft, uncrosslinked collagen matrix with VEGF and/or BMP-2, which is subsequently used to fill the open porous architecture of the scaffold. As the non-crosslinked collagen hydrogel is degraded in vivo, VEGF and/or BMP-2 will be released by the scaffold to the injury site. In vivo, protein diffusion from the hydrogel begins at day 0 and approximately 90% of the loaded protein dose is released by day 14. The encapsulation of the growth factor within the hydrogel offers several advantages. First, growth factor release is both immediate upon implantation and sustained for up to two weeks, as the collagen hydrogel is metabolized by the host, in contrast to passive adsorption onto scaffold struts which results in rapid protein release kinetic profiles. Second, the loaded protein is unmodified. Some modifications that are inherent to protein immobilization can block the active site and reduce activity. Third, encapsulation of growth factors within the hydrogel allows for a wide range of growth factor concentrations to be loaded into the scaffold.

The second mechanism utilizes a non-covalent, high affinity interaction between biotin and streptavidin (SA, $K_d = 10^{-14/-15}$ M) or other biotin-binding proteins. SA can be directly incorporated into the cross-linked collagen scaffold during preparation, providing a highly specific, high affinity binding site where biotinylated growth factors can be anchored. Due to the large dissociation constant of the biotin/SA complex, the growth factors can only be released as the collagen scaffold is enzymatically degraded in situ, enabling sustained release of the growth factors along biologically relevant timelines.

Release profiles can be tailored to mimic, accelerate or decelerate biologically relevant timelines, by adjusting the concentration of each bioactive agent and adjusting the type of mechanism used to deliver the agent to the scaffold. As described above, the scaffold can be tuned utilizing any combination of release mechanisms to optimize efficacy. As angiogenesis precedes osteogenesis during fracture healing, this approach facilitates sustained and sequential release of each agent along a desired timeline.

Scaffold System

The type of scaffold also critically impacts vascularization and osteoconduction in the defect, as well as clinical translation. HA-Col scaffolds can provide a clinically-relevant scaffold. HA-Col scaffolds are typically prepared via lyophilization, which results in the high porosity (80-99%) necessary for cellular infiltration and nutrient transport. However, lyophilized scaffolds are also limited by small pore sizes, low permeability, and poor mechanical properties with a compressive modulus typically reported between 1-250 kPa. These mechanical properties are not sufficient to enable surgical handling or fixation, nor osteogenic loading during healing.

We have prepared novel compression-molded HA-Col scaffolds, which may be tailored to possess porosity levels of 75-95%, pore diameters from 100-1000 µm, and an HA content of 0-80 vol %. These novel scaffolds also possess a compressive modulus between 200-1000 kPa, depending on the porosity level and HA content, which is an order of magnitude greater than lyophilized HA-Col scaffolds and sufficient to enable surgical handling, fixation, and osteogenic loading during healing. Furthermore, even when prepared with up to 60 vol % HA, these scaffolds are able to fully recover from deformations up to 50% strain upon cyclic loading.

Growth Factor Delivery

The release kinetics of VEGF and BMP-2 from growth factor-conjugated scaffolds can be evaluated in vitro at longitudinal time points and compared to scaffolds with passively adsorbed VEGF and BMP-2. The evaluation enables one to optimize growth factor loading strategies and ensure that biologically relevant concentrations of VEGF and BMP-2 are delivered to the targeted site following orthotopic implantation into a rat femoral segmental defect model.

Synthesis of HA-Col scaffolds containing VEGF and BMP-2

VEGF/BMP-2 Biotinylation

Biotin can be conjugated to rhBMP-2 or VEGF using conventional method. VEGF or BMP-2 can be mixed with 50 mM NaHCO$_3$ at pH 8.0 and incubated with equimolar amounts of EZ-link sulfo-NHS-biotin for 30 min at room temperature. Excess biotin can be trapped by the addition of 10 mM tris/HCl at pH 8.5 (5% v/v). Biotinylated rhBMP-2 or VEGF can be purified via mixing with monomeric avidin resin (Softlink) for 4 h at 4° C. Biotinylated rhBMP-2 or VEGF can be eluted from the monomeric avidin resin in stabilization buffer containing 5 mM biotin. Eluted biotinylated growth factors can be further purified in a 5 kDa molecular weight cut off filter (Ultrafiltration Discs, Millipore).

Figure 4:
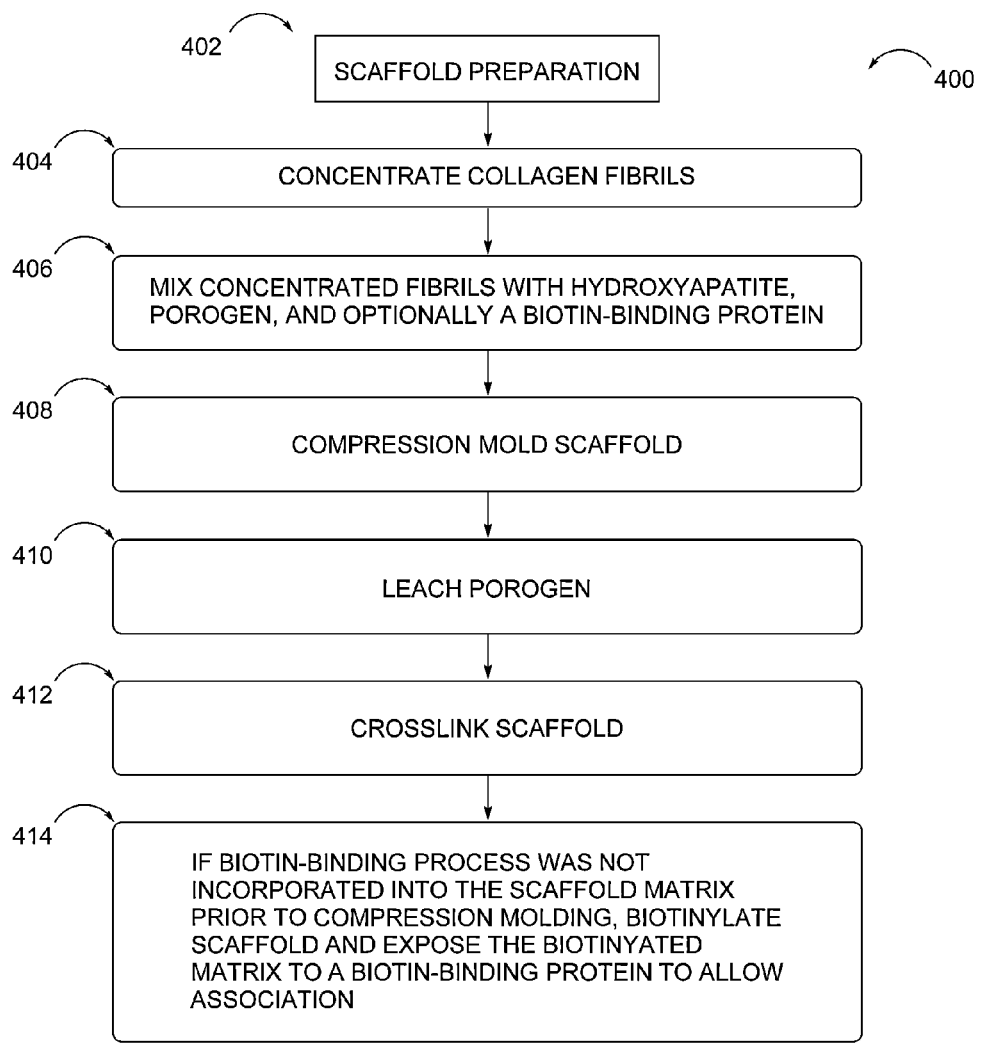
FIG. 4 illustrates a logic flow diagram for preparing a collagen scaffold prior to loading a bioactive agent into it.

SA Impregnated HA-Col Scaffolds:

FIG. 4 illustrates a logic flow diagram for preparing a collagen scaffold prior to loading a bioactive agent into it. Concentrated collagen fibrils 402 are prepared by conventional methods. Single crystal hydroxyapatite (HA) whisker reinforcements (~18×2 µm) can be prepared using a chelate decomposition method. Paraffin microspheres are a porogen 406 which can be prepared by solidifying emulsified paraffin droplets and size fractionating them to 300-425 µm using a shaker sieve. Scaffolds 402 can be prepared by mixing 406 HA whisker reinforcements in a gelled and concentrated collagen fibril slurry to achieve 40% HA whiskers by volume. An appropriate amount of porogen paraffin microspheres can be gently folded into the HA-Col slurry to prepare scaffolds with either 85% nominal porosity by volume. Optionally, a biotin-binding protein (e.g., SA) is included in the mix. Once mixed, the HA-collagen-paraffin slurry can be loaded into a 6 mm diameter pellet die and compression molded 408 at about 1 MPa for about 1 min. As molded, the scaffolds can have a height of approximately 6 mm depending on the amount of slurry added to the die. Scaffolds can be dried at 37° C. for about 24-48 hr. After drying, 3 mm diameter scaffolds can be prepared using a biopsy punch and the paraffin porogen can be leached 410 by placing scaffolds into successive solutions of 2× 100% hexane overnight, 50/50 hexane/ethanol overnight, and 4× 100% ethanol for at least 6 hr. each, with the volume of all leaching solutions being at least 20 times greater than the volume of the scaffolds. The scaffolds can be cross-linked 412 with a solution containing 20 mM 1-ethyl-3-(3-dimethylaminopropyl)carbodiimide (EDC) and 8 mM n-hydroxysuccinimide (NHS), with pH adjusted to 7.4 with 0.1 M HCl. The volume of cross-linking solution can be determined by the amount of collagen present in each scaffold. The optimum ratio of EDC and NHS to carboxyl groups in the collagen is 5:2:1 of EDC:NHS:collagen. The scaffolds are cross-linked for 12 hr. under gentle agitation using the same ratio of EDC:NHS:collagen as described above. After cross-linking, scaffolds can be washed 2× in 100% ethanol and then stored in ethanol at 4° C. until further use.

The method can be modified to accommodate the inclusion of SA 414 into the scaffold matrix to enable functionalization with biotinylated growth factors. During preparation of the collagen slurry, a collagen gel can be prepared at 37° C. overnight from soluble type I bovine collagen (DM-1, Devro Medical) at a concentration of 3.2 mg/mL in a solution of 0.01 M HCl adjusted to physiological pH and ionic strength by adding the appropriate amount of 1 M NaOH and 10× PBS. Collagen fibrils can be prepared by disrupting the gel using a tissue homogenizer and concentrated 404 by centrifugation to about 160 mg/mL. Scaffolds containing SA can be prepared by infusing SA into the collagen gel at a mass ratio of no more than about 1:1 with gelation occurring in less than 30 min.

Alternatively, if a biotin-binding protein (e.g., SA) is not incorporated into the scaffold matrix prior to compression molding, then the scaffold can be biotinylated and exposed to a biotin-binding protein 414.

Figure 5:
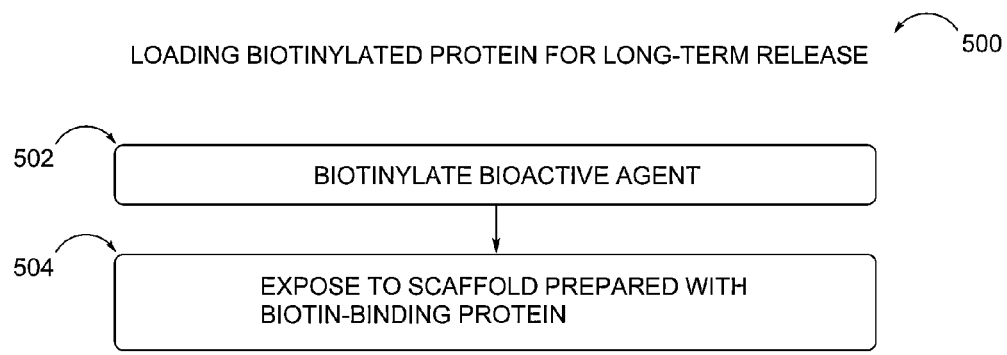
FIG. 5 illustrates a logic flow diagram for loading a long-term release biotinylated bioactive agent into a collagen scaffold.

FIG. 5 illustrates a logic flow diagram for loading a long-term release biotinylated bioactive agent into a collagen scaffold. The scaffold is prepared with a biotin-binding protein as described above. The bioactive agent is biotinylated 502 and an effective amount of the biotinylated bioactive agent is added to the scaffold 504.

Figure 6:
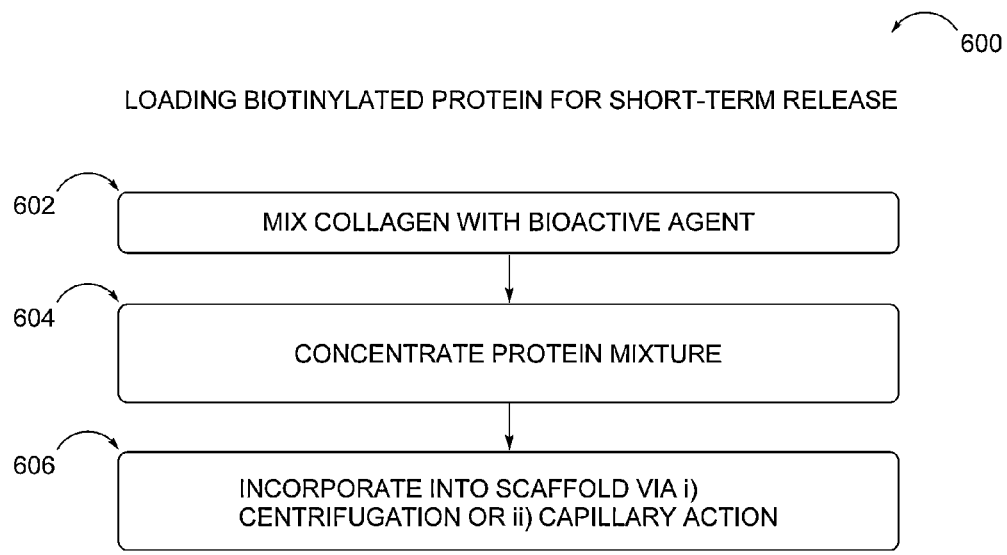
FIG. 6 illustrates a logic flow diagram for loading a short-term release biotinylated bioactive agent to a collagen scaffold.

FIG. 6 illustrates a logic flow diagram for loading a short-term release biotinylated bioactive agent to a collagen scaffold. An effective amount of bioactive agent is mixed with collagen fibrils in the scaffold 602. A biodegradable polymer, hydrogel or protein matrix is concentrated 604 and incorporated into the scaffold via centrifugation or capillary action 606.

Figure 7:
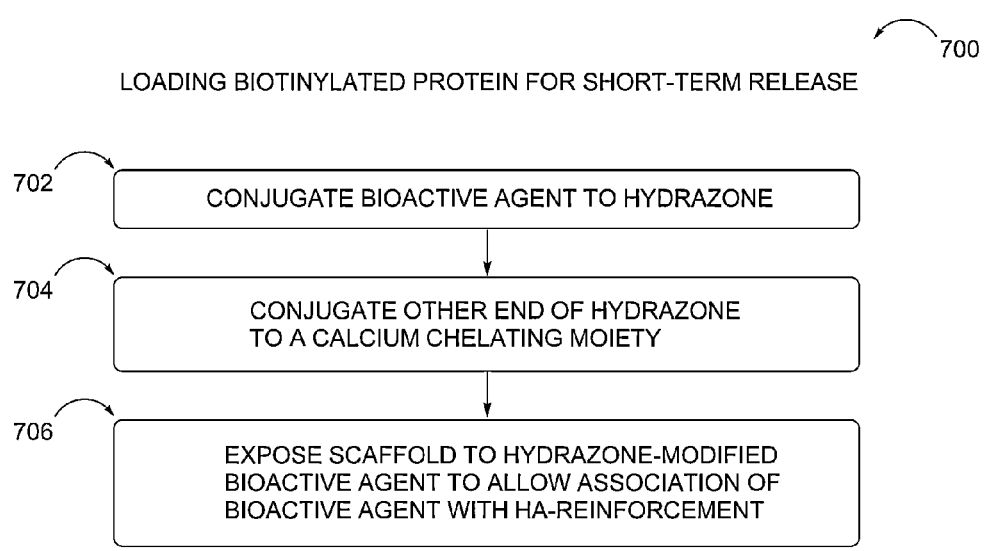
FIG. 7 illustrates an alternative logic flow diagram for loading a short-term release bioactive agent into a collagen scaffold.

FIG. 7 illustrates an alternative logic flow diagram for loading a short-term release biotinylated bioactive agent into a collagen scaffold. The bioactive agent is covalently conjugated to one terminus of a hydrazone-containing chemical compound 702. A calcium chelating moiety is covalently conjugated to the other terminus of the hydrazone-containing chemical compound 704. An effective amount of the hydrazone-conjugated bioactive agent is added to the collagen scaffold 706.

Synthesis of Protein-Impregnated Collagen Hydrogel

Soluble type 1 bovine collagen (Collagen Solutions, LLC) at a concentration of 3.2 mg/mL in 0.01 M HCL can be neutralized via addition of an appropriate amount of 1 M NaOH. The pH and ionic strength can be raised to physiological values, 7.4 and 0.05 M, respectively, via the addition of 10× PBS. The desired amount of VEGF and rhBMP-2 can be added to the collagen solution and gently vortexed to ensure uniform distribution of the protein throughout the hydrogel.

Growth Factor Loading

Biotinylated BMP-2 and VEGF can be added drop-wise to the scaffolds to achieve an appropriate molar ratio to bind with the SA incorporated into the scaffolds. Total loaded doses of BMP-2 and VEGF are between about 1.0 µg/scaffold and 2.0 µg/scaffold. Following conjugation with the biotinylated protein, the collagen-growth factor solution can be added drop-wise to the scaffolds, and the hydrogel can be impregnated by capillary action. The SA:collagen ratio, growth factor solution concentrations, and incubation times can be varied to optimize the effects on growth factor loading.

Growth factor conjugation can be quantified via hydrogen/deuterium exchange, quenching, pepsin digestion of the scaffold, and analysis of digested samples by mass spectroscopy in comparison to scaffolds not exposed to any growth factors, biotinylated growth factors not exposed to scaffolds, and scaffolds exposed to unbiotinylated growth factors. The amount of VEGF and BMP-2 either conjugated or adsorbed within the scaffolds can also be quantified by measuring supernatant concentrations via ELISA after scaffold digestion in collagenase.

Col-HA scaffolds with 85% porosity and 40% vol % HA whiskers were also impregnated with a soft collagen hydrogel using the methods described above. The hydrogel was able to penetrate to the center of the scaffold, filling all available pore space.

Biotinylated growth factors can bind to the SA in the scaffold and remain stably bound to the scaffold until the scaffold is digested in vivo by infiltrating cell populations. Mass spectroscopy can demonstrate functionalization with biotin and the stable conjugation of the biotinylated growth factors to the scaffold surface. ELISA can verify the presence of biotinylated growth factors upon in vitro digestion of the scaffolds with collagenase.

Growth factor biotinylation can be performed via commercially available kits (Pierce). Hydrogel impregnation of collagen scaffolds relies upon centrifugation to ensure penetration of the viscous hydrogel to the center of the scaffold prior to gelation in situ. The method is reliable for low viscosity hydrogels. If hydrogel permeation does not sufficiently occur with increased hydrogel viscosity, alternative techniques can be utilized, such as vacuum assisted capillary action. Alternatively, scaffolds can be prepared having larger pore diameters to ease infiltration.

Biotinylated Growth Factor Activity

An assay can be run to verify growth factor activity after biotinylation. A human osteosarcoma cell line (MG-63, ATCC) can be cultured in McCoy's 5a Medium Modified supplemented with 15% fetal bovine serum (FBS) and 1% penicillin/streptomycin, per conventional methods. MG-63 cells can be cultured along with 100 ng/mL of either biotinylated VEGF, unmodified VEGF, biotinylated BMP-2 or unmodified BMP-2 for 7 days. ELISA can be utilized to measure the presence of proteins up-regulated when either BMP-2 or VEGF binds to extracellular receptors. In the case of VEGF, the production interleukin-6 (IL-6), an inflammatory cytokine, is increased. In the case of BMP-2, the production of osteopontin is increased. These two biological molecules serve as appropriately specific targets to determine the relative activity of the biotinylated growth factor as compared to the unmodified growth factor. This approach is non-quantitative, but can verify growth factor activity.

Growth Factor Release Kinetics

Scaffolds prepared as described above with either conjugated or adsorbed growth factors can be re-suspended in 5 mL of 0.1% BSA in PBS at 37° C. Aliquots can be taken from the supernatant and the concentration of BMP-2, VEGF and BSA in the buffer can be measured via ELISA at longitudinal time points until no increase in the protein concentration of the supernatant can be detected. After the final time point, scaffolds can be digested in 0.1 mg/mL collagenase for 12 h to measure residual protein via ELISA.

In Vitro Scaffold Osteogenicity:

The scaffolds prepared with either conjugated and encapsulated growth factors (n=3/time point), adsorbed growth factors (n=3/time point), or without growth factors (n=3/time point) can be cultured with murine adipose stromal cells (mASCs) seeded at a density of $10^5$ cells/cm$^3$ in osteogenic media (DMEM, 10% FBS, 1% pen/strep, 10 nM β-glycerophosphate, 50 µg/mL ascorbic acid) for 21 days. Scaffolds can be embedded in OCT and fresh frozen at days 1, 7, 14, and 21. Culture medium can be removed at days 1, 7, 14, and 21 and the concentration of VEGF and BMP-2 released from the scaffold can be determined via ELISA. Scaffolds can be sectioned and stained with H&E, for alkaline phosphatase, or immunostained for osteocalcin and osteopontin.

Growth factor release can be sustained over a longer time period for scaffolds containing conjugated and hydrogel encapsulated protein as compared to passively adsorbed protein. Based on these results, loading mechanisms and loaded doses can be adjusted to optimize release kinetics for osteogenesis and to imitate physiological release timelines.

Cells cultured on scaffolds with growth factors can produce more osteocalcin and osteopontin than cells cultured on scaffolds without growth factors. Cells cultured on scaffolds with either adsorbed or conjugated/encapsulated growth factors can perform similarly at early time points. However, by day 21, cells cultured on scaffolds with conjugated/encapsulated growth factors can be more osteogenic than cells cultured on scaffolds with adsorbed growth factors. Further, BMP-2 and VEGF concentrations in the culture medium can remain elevated at later time points for cells cultured on scaffolds with conjugated/encapsulated growth factors as compared to cells cultured on scaffolds with adsorbed growth factors.

If a quantitative determination of growth factor activity is necessary due to a significant decrease in protein activity after modification, a more complicated method can be utilized to determine the percentage of protein still active. Briefly, vectors can be constructed containing a BMP-2/VEGF Responsive Element (BRE/VRE), a luciferase gene (LUC), and a neomycin resistance gene (Neo) to create the pNeo-(BRE/VRE)$_2$-LUC vector. Mouse myocyte cells can be grown in DMEM supplemented with 10% fetal calf serum and antibiotics. Cells seeded at $8×10^4$ cells/well in a 35 mm dish for 24 h can then be stably transfected with 1 µg pNeo-(BRE)$_2$-LUC using Lipofectamine. Cells can then be reseeded after 24 hr. and selected for antibiotic resistance with 700 µg/ml geneticin. Resistant colonies can be isolated, expanded and tested in the reporter cell assay.

For the assay, growth factor-sensitive clones can be seeded in 96 well plates at densities of $4×10^3$ cells/well and allowed to attach overnight. The medium can be replaced with medium containing biotinylated growth factor and unmodified growth factor. After 14 hr., the cells are washed twice with PBS and cell extracts which are prepared with 45 µl of 1× cell lysis buffer. 35 µl of the cell lysate are transferred to a 96-well microplate and assayed for luciferase activity. The cells will remain responsive to the growth factor for up to about 10 passages.

Alternatively, cloning a growth factor reporter into an established cell can allow for quantification of the modified growth factor activity compared to the unmodified growth factor.

In the event the biotinylated growth factor activity is significantly decreased as compared to unmodified growth factors, less dense biotinylation can be achieved via a sulfhydryl mechanism.

Surgical Procedure

Bone formation can be investigated using conventional preclinical femoral segmental defect model in rats. Scaffolds can be prepared as described above with 40 vol % HA and 85 vol % porosity. Optimal growth factor loading concentrations can be used to prepare experimental groups with loading mechanisms as specified (n=5/group). Scaffolds can be implanted within a critically-sized 5 mm mid-diaphyseal defect in the femur of anesthetized Wistar rats. Internal fixation can be achieved using a customized PEEK plate attached to the distal and proximal femur via screws to maintain stability during the osteotomy and healing.

Micro-CT Evaluation

Scaffolds can be imaged longitudinally at 0, 4 and 8 weeks after implantation by in vivo micro-CT on anesthetized rats (Bioscan NanoCT) at 80 µm resolution along with a BMD phantom. Bone formation can be measured as the difference in segmented bone volume between a given time point and day 0.

Histology

Rats can be euthanized and grafts harvested 8 weeks after implantation. Two explants from each experimental group can be fixed in 4% buffered formalin, decalcified in 0.5 M EDTA at pH 8 for 7-10 days, paraffin embedded, sectioned (5 µm thick), and stained with H&E and modified Masson's Trichrome to identify fibrous tissue, bone matrix and the scaffold under microscopy. Three explants from each experimental group can be embedded in OCT and fresh frozen. Sections from fresh frozen tissue can be stained for 1 hr. by TRAP (0.5 mg/mL naphthol AS-MX phosphate and 1.1 mg/mL Fast red violet LB in TRAP buffer prewarmed to 37° C.) after incubating in TRAP buffer (50 mM sodium acetate, 30 mM sodium tartrate, 0.1% Triton X-100, pH 5) for 20 min and then washed twice in PBS, counterstaining with hematoxylin, and mounted on glass slides. Immunostaining for CD31 can be performed to indicate regions of high vascularity, which are useful in evaluating implant performance at earlier sacrifice time points. Immunostaining for osteocalcin and osteopontin can be performed to help identify regions with osteoblast activity.

We have tested the novel scaffolds described herein without growth factors. We evaluated osteogenesis in scaffolds implanted in an ectopic murine model. No growth factors were present in the scaffolds. The bone volume measured by micro-CT increased with increasing HA content, and from pre-implantation to post-implantation in all Col-HA scaffolds at 6 and 12 weeks, but was not significantly increased in collagen scaffolds.

All scaffold explants exhibited complete cellular infiltration and significant matrix deposition after 6 weeks implantation. At 6 weeks, scaffolds prepared with 40 vol % HA, no matter whether processed in PBS or FBS, exhibited dense cell populations and matrix deposition, as well as vascularization. Scaffolds with less than 40 vol % HA exhibited no evidence of angiogenesis. Collagen scaffolds exhibited smaller cell populations and less dense matrix deposition compared to Col-HA scaffolds. By 12 weeks, the porous architecture of scaffolds with 40 vol % HA was rearranged by infiltrating cells. In contrast, the original scaffold architecture was mostly maintained at 12 weeks in collagen scaffolds. By 12 weeks, regions of the scaffold that were vascularized maintained healthy cell populations, while regions without vasculature exhibited a decrease in cell number in both collagen and Col-HA scaffolds. Scaffolds removed from ectopic, in vivo sites have been successfully stained to determine general tissue morphology with H&E and Masson's Trichrome. Immunostaining and TRAP staining may also be undertaken.

The osteogenic potential of the scaffolds without adsorbed growth factors has been investigated in a critical size defect in an orthotopic rat model. Scaffolds with 40 vol % HA showed a statistically significant increase in bone volume compared to other scaffold groups. Bone formation was observed after 10 weeks in vivo in implanted 40% HA, 85 vol % porosity scaffolds. Osteogenesis was not observed in implanted 0% HA, 85 vol % porosity scaffolds or empty defects Col-HA scaffolds which enable sequential, sustained delivery of VEGF and BMP-2 can regenerate increased bone in critical size defects as compared to Col-HA scaffolds with adsorbed growth factors. Histology can confirm micro-CT results, demonstrating increased bone quantity and increased bone quality in experimental groups implanted with Col-HA scaffolds, which enable sequential and sustained release of VEGF and BMP-2 as compared to empty defects and scaffolds with adsorbed growth factors. Further, Col-HA scaffolds that enable sequential and sustained release can also exhibit increased vascularity at both early and late sacrifice time points, a result that will not be apparent via micro-CT.

Surgical technique and an understanding of the necessary number and location of fracture fixation anchors to ensure fracture stability can mediate unstable fracture fixations, which could lead to impaired bone formation due to disruption of angiogenesis. Alternative approaches can also be taken for fixation of segmental femoral defects in rats. Quantification of increased bone mass requires appropriate thresholding and exact image registration. Thresholding can be determined by pre-implantation scans, based on the necessary minimum attenuation that corresponds with the known percentage of HA present in the scaffold. Images can be registered based on the location of fixation screws.

The scaffolds and growth factor delivery methods described herein provide a highly flexible platform from which to optimize bone regeneration. Bone regeneration can be optimized by investigating varying growth factor doses loaded and released via each mechanism in order to further fine-tune release profiles. Optimal in vivo loaded growth-factor dosing can be determined for each mechanism by quantifying bone formation for conjugated and hydrogel-encapsulated growth factors at varying doses of loaded growth factor.

Using a rat segmental femoral defect model, scaffolds can be implanted which have growth factors adsorbed. Scaffolds with both conjugated and impregnated VEGF and BMP-2 can form extensive vasculature and osteoid. Scaffolds without growth factors will not form bone or vasculature. Scaffolds which utilize different loading mechanisms for each growth factor can enable sequential, sustained delivery of VEGF and BMP-2 and regenerate increased vasculature in bone in critical size defects as compared to Col-HA scaffolds with adsorbed growth factors. Further, higher total loaded doses of growth factors can result in increased vasculature and bone formation. Histology can confirm and support micro-CT results, demonstrating increased bone quantity and increased bone quality in experimental groups implanted with Col-HA scaffolds, enabling sequential and sustained release of VEGF and BMP-2 as compared to empty defects and scaffolds with adsorbed growth factors.

While specific embodiments have been described above with reference to the disclosed embodiments, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A tunable tissue scaffold comprising a matrix and at least two bioactive agents comprising A and B,
   wherein:
   (a) (i) the bioactive agent A is biotinylated,
       (ii) the matrix is biotinylated, and
       (iii) the biotinylated bioactive agent A and the biotinylated matrix are conjugated to one another via a biotin-binding protein to form a linkage comprising bioactive agent A-biotin-biotin-binding protein-biotin-matrix;
   and
   (b) the bioactive agent B is delivered to the matrix by
       (i) conjugation and a pH labile covalent linkage, or
       (ii) non-conjugation and passive adsorption; and
   wherein the bioactive agent B is released from the matrix over a shorter timeline than the bioactive agent A.

2. The scaffold of claim 1 wherein the biotin-binding protein is selected from the group consisting of streptavidin, avidin, neutravidin, and non-glycosylated, tetrameric biotin-binding proteins.

3. The scaffold of claim 1 wherein the pH labile covalent linkage comprises a hydrazone linkage for conjugation of the bioactive agent B to a calcium-chelating moiety.

4. The scaffold of claim 1 wherein the non-conjugated bioactive agent B is encapsulated within a biodegradable polymer, hydrogel, or protein matrix.

5. The scaffold of claim 1 wherein the at least two bioactive agents are selected from the group consisting of vascular endothelial growth factors (VEGFs), bone morphogenetic proteins (BMPs), insulin-like growth factors (IGFs), fibroblast growth factors (FGFs), transforming growth factor beta (TGF-β), platelet-derived growth factors (PDGFs), nerve growth factors (NGFs), connective tissue growth factors (CTGFs), and epidermal growth factors (EGFs).

6. The scaffold of claim 5 wherein the at least two bioactive agents are BMP-2 and VEGF.

7. The scaffold of claim 6 wherein bioactive agent A is BMP-2 and bioactive agent B is VEGF.

8. The scaffold of claim 6 comprising about 0.1 μg to 100 μg of each bioactive agent.

9. The scaffold of claim 7 wherein BMP-2 is released from the matrix in vivo over a biologically relevant timeline extending from between about 7 and 56 days, and VEGF is released from the matrix in vivo over a biologically relevant timeline extending from between about 1 and 28 days.

10. The scaffold of claim 9 wherein the peak release of BMP-2 from the matrix in vivo occurs between about 21 and 28 days, and the peak release of VEGF from the matrix in vivo occurs between about 10 and 14 days.

11. The scaffold of claim 1 wherein the matrix comprises cross-linked collagen fibrils and about 0-80 vol % of calcium phosphate reinforcements.

12. The scaffold of claim 11 wherein the matrix comprises about 20-60 vol % of calcium phosphate reinforcements.

13. The scaffold of claim 11 wherein the calcium phosphate reinforcements are hydroxyapatite reinforcements, β-tricalcium phosphate reinforcements or a mixture thereof.

14. The scaffold of claim 11 wherein the calcium phosphate reinforcements are spheres, whiskers or a mixture thereof.

15. The scaffold of claim 9 wherein the matrix has a porosity of about 65-99 vol %, pore diameters of about 100-1000 μm, and a compressive modulus of greater than about 100 kPa.

16. The scaffold of claim 15 wherein the matrix has a porosity of about 75-95 vol %, pore diameters of about 200-600 μm, and a compressive modulus of about 200-1000 kPa.

17. A tunable tissue scaffold comprising a matrix and at least two bioactive agents comprising vascular endothelial growth factor (VEGF) and bone morphogenetic protein 2 (BMP-2), wherein the matrix comprises cross-linked collagen, hydroxyapatite reinforcements, and a biotin-binding protein;
   wherein:
   (a) (i) BMP-2 is biotinylated,
       (ii) the matrix is biotinylated, and
       (iii) the biotinylated BMP-2 and the biotinylated matrix are conjugated to one another via the biotin-binding protein to form a linkage comprising BMP-2-biotin-biotin-binding protein-biotin-matrix;
   and
   (b) VEGF is delivered to the matrix by
       (i) conjugation via a hydrazone linkage to a calcium-chelating moiety selected from the group consisting of glutamic acid and bisphosphonates, or
       (ii) encapsulation within a biodegradable polymer, hydrogel, or protein matrix; and
   wherein VEGF is released from the matrix over a shorter timeline than BMP-2.

18. A method of enhancing repair and/or regeneration of tissue or bone in a patient in need thereof comprising introducing the scaffold of claim 1 into a tissue or bone in need of treatment in the patient.

* * * * *